US00PP09753P

United States Patent [19]

Martin et al.

[11] Patent Number: Plant 9,753

[45] Date of Patent: Dec. 17, 1996

[54] AVOCADO TREE CALLED LAMB/HASS

[75] Inventors: Gray E. Martin, Moreno Valley; Berthold O. Bergh, Riverside, both of Calif.

[73] Assignee: The Regents of the University of California, Oakland, Calif.

[21] Appl. No.: 483,610

[22] Filed: Jun. 7, 1995

[51] Int. Cl.[6] ..... A01H 5/00

[52] U.S. Cl. ..... Plt./44

[58] Field of Search ..... Plt./44

[56] References Cited

U.S. PATENT DOCUMENTS

P.P. 139 8/1935 Hass ..... Plt./44

*Primary Examiner*—James R. Feyrer

*Attorney, Agent, or Firm*—Townsend and Townsend and Crew

[57] ABSTRACT

A new and distinct variety of avocado tree characterized by its production capacity similar to 'Gwen', i.e., greater than 'Hass' and a season similar to 'Gwen', i.e., later maturing than 'Hass'. The skin color and texture is like that of its "Great-grandparent," 'Hass', and flavor is rated good to very good.

3 Drawing Sheets

DESCRIPTION

This invention relates to a new and distinct variety of avocado tree (*Persea americana*), designated 'Lamb/Hass'.

'Lamb/Hass' is a seedling selection from an open pollinated breeding cross with the 'Gwen' avocado cultivar (U.S. Plant Pat. No. 5,298) as the maternal parent. The 'Gwen' variety has been described as a "grandchild" of 'Hass', the currently dominant commercial avocado in both California and the world.

'Lamb/Hass' has been asexually propagated by grafting budwood onto rootstocks in the nursery and directly in the field.

'Lamb/Hass' was first asexually propagated on the Ventura County Camarillo Ranch of Robert Lamb, L Block, trees 109 and 116 in May of 1989.

'Lamb/Hass' has several distinguishing characteristics which make it commercially valuable. For example, its appearance is uniquely similar to 'Hass' and consumers will identify 'Lamb/Hass' as a 'Hass' type avocado. In addition, the performance of 'Lamb/Hass' exceeds that of 'Hass'. Data collected from several sites, including University of California property and commercial groves show that the new variety continuously yields an increase of 50% above 'Hass'. Statistical documentation of yield is approximately four years from early completion but is currently in progress with respect to 'Lamb/Hass'. Another feature of 'Lamb/Hass' is that its season of maturity is later in the year than 'Hass'. This means the growers will have the option of extending 'Hass'-type production of avocados throughout the year and to obtain the affiliated benefits of extending the production season.

Early indications are that 'Lamb/Hass' has at least some resistance to the industry's newest and most severe pest, namely, persea mite.

In the drawings

SPECIFIC DESCRIPTION

Fruit

Figure 1:
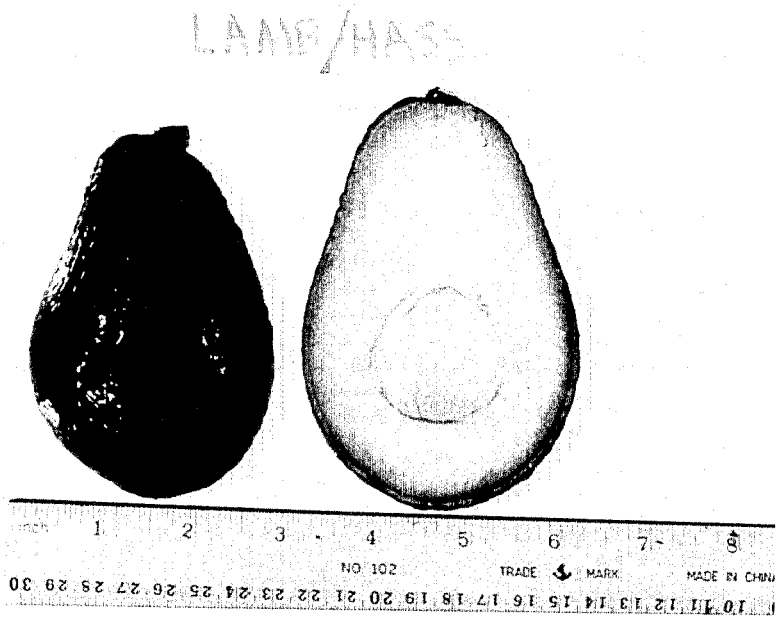
FIG. 1 shows a frontal and side view typical of the fruit of 'Lamb/Hass'. Cut fruit with seed is illustrated with uncut fruit showing black finely-pebbled skin.
Figure 2:
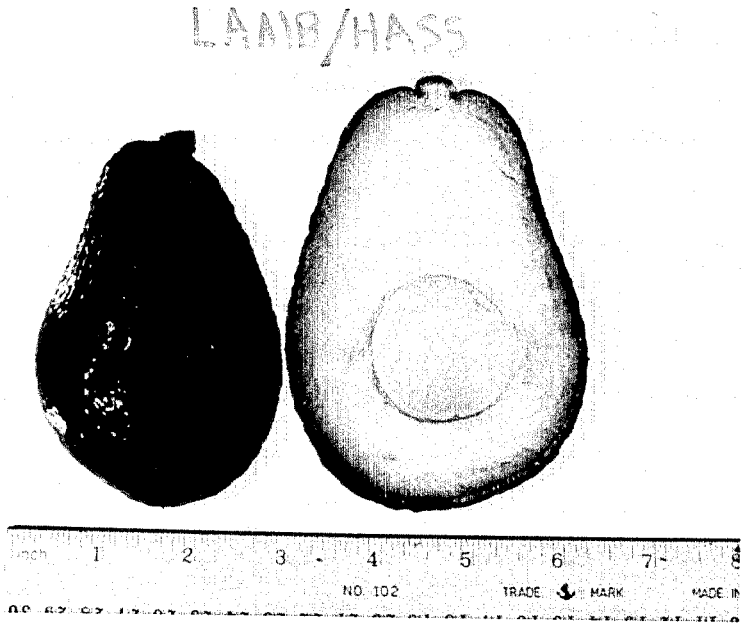
FIG. 2 shows cut and uncut fruit typical of the 'Lamb/Hass' variety and illustrates the variable shapes of the fruit.
Figure 3:
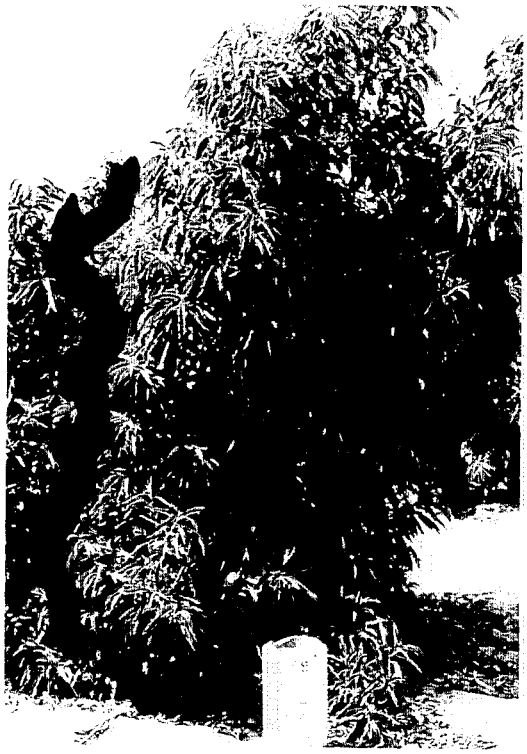
FIG. 3 illustrates a typical tree of the 'Lamb/Hass' variety and shows a tree more columnar and denser than that of the 'Hass' variety.
Figure 4:
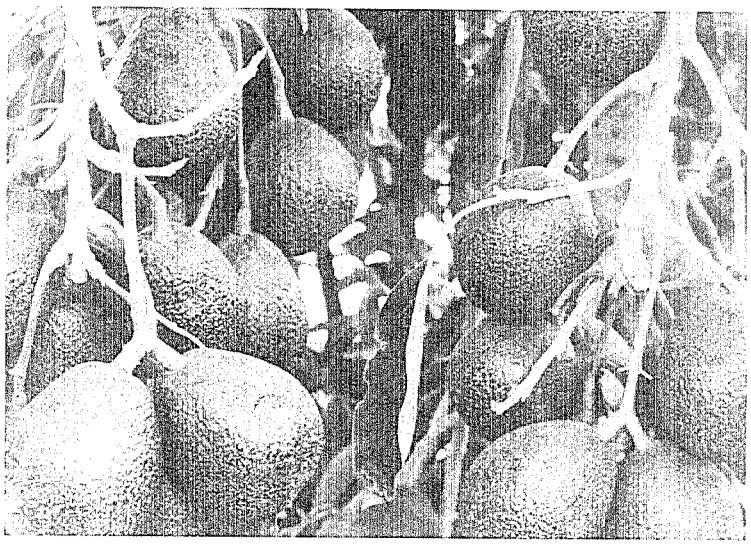
FIG. 4, shows the heavy clustered set of the fruit of new variety.
Figure 5:
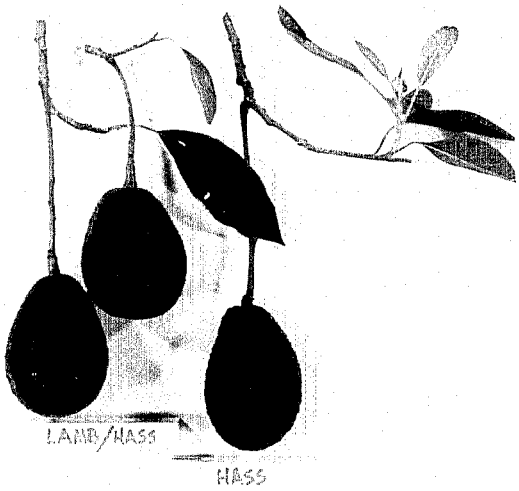
FIG. 5 and FIG. 6 depict typical fruit of 'Lamb/Hass' and 'Hass' and illustrate the less elongate shape of the fruit of 'Lamb/Hass' as compared with 'Hass'.
Figure 6:
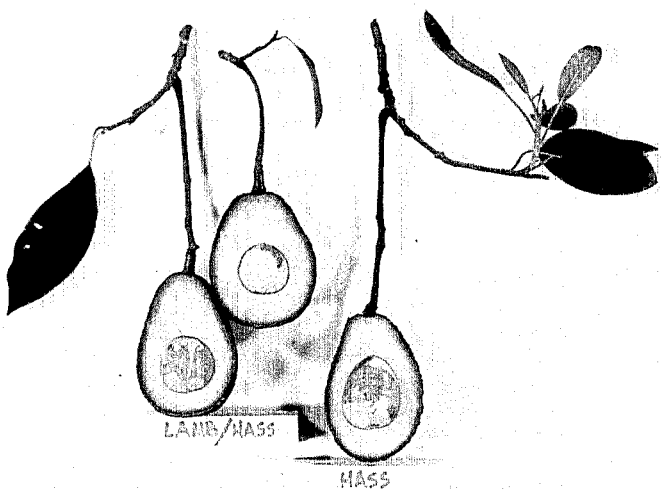

Fruit is pear shape with a distinctive flat top or a flat "shoulder." Ripe fruit color is black, and unripe fruit is green mostly indistinguishable from 'Hass'. The fruit size varies with crop size, but is typically larger than 'Hass' relative to yield (280–320 grams). Fruit shape varies in all avocados with distance from the ocean and from fruit to fruit on a given tree. 'Lamb/Hass' and 'Hass' will thus have overlapping fruit shapes. Fruit size also overlaps among 'Lamb/Hass' and 'Hass'. Combining this with the joint black ripe skin color, 'Lamb/Hass' will be able to capitalize on the market recognition of the 'Hass' variety which is now dominant in the industry. 'Lamb/Hass', based upon 1995 production results had a range of yield of 29–198 fruits per tree with a mean of 108. The 'Hass' range was 0–49 fruits per tree with a mean of 31 and the fruits were smaller than 'Lamb/Hass'. Further, 'Lamb/Hass' produced a commercial crop just two years from planting which is considered remarkable for avocados. The roughness of the skin is finely-pebbled, typically less rough than 'Hass', otherwise very similar. Russeting is almost nonexistent. The skin thickness is medium-plus, thicker than 'Hass' and slightly less pliable—more often breaking when peeled back from the flesh, as compared with 'Hass'. The peel separation from the flesh is clean, similar to 'Hass'. The flesh color is virtually identical with 'Hass'. The flesh fibers are both common and pronounced as compared to 'Hass', particularly in small-sized fruit. The seed size and adherence to flesh is similar to 'Hass'. Overall, the flesh quality is "good". In the 'Hass' "late" season, the quality of 'Lamb/Hass' relative to 'Hass' is "very good." 'Lamb/Hass' has a less rich, milder flavor than 'Hass.' Flavor is considered inferior to 'Hass' by some consumers while considered superior by others. In oil content, initial data indicate that 'Lamb/Hass' is about ⅔ of the 'Hass' level early in the season (March–May) increasing to about ¾ of 'Hass' in July and then, as 'Lamb/Hass' reaches its later prime about September, it is about 9/10 of the oil content of 'Hass'. Two seasons of preliminary post-harvest fruit storage data suggest that 'Lamb/Hass' compares equally with the 'Hass' standard.

Tree and Foliage

Individual differences in tree form and leaf foliage are frequently subtle and generally nondescript. 'Lamb/Hass' is said to exhibit upright tendencies, at least more so than 'Hass', but this can be substantially influenced by pruning. Like 'Hass', 'Lamb/Hass' is a vigorous grower more so than its parent 'Gwen'. Under conditions where the 'Hass' tree might have a height and spread of 8 m, 'Lamb/Hass' might be 7 m tall and 5 m wide. Branching of 'Lamb/Hass' is quite similar to 'Hass' including major scaffolds. Tree bark is also not discriminative. Water sprouts are not a phenomenon of normal, healthy avocado trees. The canopy density of 'Lamb/Hass' is greater than that of 'Hass'. Excessive pruning does not induce wild branching. The leaf color of 'Lamb/Hass' is distinctly darker than 'Hass', resembling varieties like 'Bacon' and 'Reed', the third and fourth leading commercial cultivars. Young leaf anthocyanin pigment is present varying from light to moderate. Leaf color of 'Lamb/Hass' varies widely with leaf age, location on the tree, light exposure and individual nutrition. The typical immature leaf according to The Horticultural Colour Chart, Wilson Colour, Ltd., would be lettuce green, 861/2 with commonly a reddish-brown overlay. For immature leaves, 'Hass' averages spinach green, 000960. 'Lamb/Hass' is darker than 'Hass' averaging ivory green 0001060/2. Leaf shape is elliptical to slightly ovate with acute tips. 'Lamb/Hass' leaves have an acute base whereas 'Hass' is slightly more obtuse. Anise fragrance has not been detected in the stems or leaf. Pedicels (fruit stalks) are cylindrical to slightly conical, with no "nail head" flange at the point of attachment. Average pedicel length and width is 7×1 cm. The pedicel point of attachment is centrally located on the apex of the fruit, more so than 'Hass'. The flower type is 'A', the same as 'Hass', and bloom is similarly timed in spring. Inflorescences are not helpfully different between 'Lamb/Hass' and 'Hass'. Fruit set frequently occurs in clusters and is evenly distributed throughout the tree. Production occurs more regularly, less alternate, than 'Hass'. Fruit stems are exceptionally short in 'Lamb/Hass' (about 7 cm) and shorter than the average stems of 'Hass'. Otherwise the stems of the two varieties are similar. Only the stub of a stem is depicted in the drawing because the rest has been cut off as is normally done with commercial fruits.

Skin Color

It is impossible to assign very meaningful distinctions of 'Lamb/Hass' based upon color of skin. The basic green skin color of unripe fruit not only varies of itself but differs as to the time of fruit set and location on the tree and according to geographic location and the degree of maturity. 'Lamb/Hass' fruit skin turns dark purple upon ripening and, therefore, is referred to in the trade as "black" or 'Hass'-like. The skin of avocado fruits of 'Lamb/Hass' becomes deeper green as the fruits develop, and are a spinach green, 000960 at maturity, close to the color of a mature 'Hass' leaf. 'Lamb/Hass' and 'Hass' have fruit which is commonly green when picked; unlike other commercial California avocados, 'Lamb/Hass' fruits turn black as they ripen to edible softness as does 'Hass'.

Pests and Disease

With respect to pests and diseases not previously described, 'Lamb/Hass' is no more nor less susceptible than standard 'Hass'. The same is also true with respect to cold injury, with both varieties classified as "tender". The mother tree and two select grafted trees have been shown to be free of the viroid "Sublotch", as determined by the California State Department of Agriculture, through a procedure referred to as "indexing".

We claim:

1. The new and distinct variety of avocado tree herein described and illustrated and identified by the characteristics enumerated above.

* * * * *